United States Patent [19]

Seitz et al.

[11] Patent Number: 5,158,962

[45] Date of Patent: Oct. 27, 1992

[54] FUNGICIDAL SUBSTITUTED AMINO ACID AMIDES

[75] Inventors: Thomas Seitz, Monheim; Detlef Wollweber, Wuppertall; Wilhelm Brandes, Leichlingen, all of Fed. Rep. of Germany

[73] Assignee: Bayer Aktiengesellschaft, Leverkusen, Fed. Rep. of Germany

[21] Appl. No.: 591,912

[22] Filed: Oct. 2, 1990

[30] Foreign Application Priority Data

Nov. 1, 1989 [DE] Fed. Rep. of Germany ....... 3936298

[51] Int. Cl.⁵ ..................... A01N 43/40; A01N 37/00; A01N 43/08; C07D 213/62

[52] U.S. Cl. ................................... 514/335; 514/351; 514/357; 514/461; 514/473; 514/506; 546/261; 546/300; 546/334; 549/472; 549/479; 549/491; 560/163

[58] Field of Search ................ 560/163; 514/506, 351, 514/335, 357, 461, 473; 546/261, 300, 334; 549/472, 479, 491

[56] References Cited

FOREIGN PATENT DOCUMENTS 0398072 5/1990 European Pat. Off. ............ 560/163
0425925 10/1990 European Pat. Off. ............ 560/163
0873049 7/1961 United Kingdom ................ 560/163

OTHER PUBLICATIONS

Chemical Abstracts, vol. 109, No. 11, Sep. 12, 1988.

Primary Examiner—Mary C. Lee
Assistant Examiner—Joseph K. McKane
Attorney, Agent, or Firm—Sprung, Horn, Kramer & Woods

[57] ABSTRACT

Fungicidal substituted amino acid amides of the formula

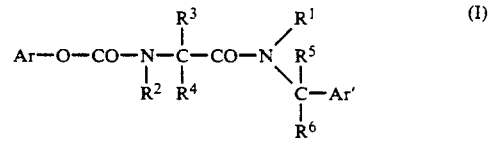

in which

Ar and Ar' are identical or different and represent unsubstituted or substituted aryl, unsubstituted or substituted aralkyl, unsubstituted or substituted heteroaryl and unsubstituted or substituted heteroarylalkyl, and $R^1$, $R^2$, $R^3$, $R^4$, $R^5$ and $R^6$ are identical or different and represent hydrogen or alkyl or $R^3$ and $R^4$, together with the carbon atom to which they are bonded, form a cycloalkyl ring.

7 Claims, No Drawings

FUNGICIDAL SUBSTITUTED AMINO ACID AMIDES

The present invention relates to new substituted amino acid amide derivatives and to a process for their preparation, and also to their use in pest-combating agents.

The substances according to the invention have an excellent action in the combating of pests. In particular, the substances according to the invention can be used as fungicides, above all in plant protection.

Certain amino acid amides are already known, such as, for example, N-tert.-butoxycarbonyl-L-leucylbenzylamide (EP-A-236,874).

However, use of these compounds in pest-combating agents has not been described.

The subject matter of the present application are thus new amino acid amide derivatives of the general formula (I)

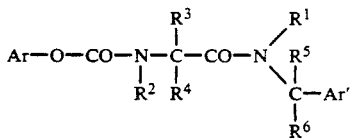

in which

Ar and Ar′ are identical or different and represent unsubstituted or substituted aryl, unsubstituted or substituted aralkyl, unsubstituted or substituted heteroaryl and unsubstituted or substituted heteroarylalkyl, $R^1$, $R^2$, $R^3$, $R^4$, $R^5$ and $R^6$ are identical or different and represent hydrogen or alkyl or $R^3$ and $R^4$, together with the carbon atom to which they are bonded, form a cycloalkyl ring.

The compounds of the formula (I) may additionally contain one or more chiral centers and may thus be present in various enantiomer and diastereomer mixtures which can be separated, if desired, in a customary manner. Both the pure enantiomers and diastereomers, as well as the mixtures, are claimed according to the invention.

In the following, compounds of the formula (I) are always referred to for the sake of simplicity, although both the pure compounds and the mixtures with different proportions of isomeric, enantiomeric and diastereomeric compounds are meant.

Formula (I) provides a general definition of the substituted amino acid amide derivatives according to the invention.

The following preferably have the meanings below in the general formulae, if not defined otherwise: alkyl, individually or in combined radicals —straight-chain or branched alkyl having 1 to 6, in particular 1 to 4 carbon atoms. Methyl, ethyl, n—and i -propyl, and n.-, i.-, s.- and t.-butyl may be mentioned by way of example and in preference.

Aryl unsubstituted or substituted aryl having 6 to 10 carbon atoms. Phenyl and naphthyl, in each case unsubstituted or substituted, in particular unsubstituted or substituted phenyl may be mentioned by way of example and in preference.

Aralkyl unsubstituted or substituted aralkyl having 1 to 4, in particular 1 or 2 carbon atoms in the straight-chain or branched alkyl moiety and 6 to 10 carbon atoms, preferably phenyl in the aryl moiety. Benzyl, 1,1- and 1,2-phenethyl and 1,1-, 1,2-, 1,3- and 2,2-phenylpropyl may be mentioned by way of example and in preference.

Heteroaryl an unsubstituted or substituted 5- to 9-membered ring, in particular a 5- to 7-membered ring, which contains 1 to 4, preferably 1 to 3, identical or different hetero atoms. Hetero atoms which may be mentioned in preference are oxygen, sulphur and nitrogen. Pyrimidinyl, pyrrolyl, isothiazolyl, oxazolyl, thienyl, furyl, pyridazinyl, pyrazinyl, isooxazolyl, thiazolyl and, in particular, pyridyl may be mentioned by way of example and in preference.

Heteroarylalkyl the heteroaryl moiety corresponds to the abovementioned definitions and ranges of preference. The alkyl moiety is straight-chain or branched and contains 1 to 4, in particular 1 or 2,carbon atoms. Heteroarylmethyl, 1,1-and 1,2-heteroarylethyl and 1,1-, 1,2-, 1,3- and 2,2-heteroarylpropyl may be mentioned by way of example and in preference.

The optionally substituted radicals of the general formulae may carry one or more, preferably 1 to 3, in particular 1 or 2, identical or different substituents. Substituents which may be mentioned by way of example and in preference are: alkyl preferably having 1 to 4, in particular 1 or 2 carbon atoms, such as methyl, ethyl, n - and i -propyl and n -, i - and t -butyl; alkoxy preferably having 1 to 4, in particular 1 or 2 carbon atoms, such as methoxy, ethoxy, n - and i -propyloxy and n -, i -, sec - and t -butyloxy; alkylthio preferably having 1 to 4, in particular 1 or 2 carbon atoms, such as methylthio, ethylthio, n - and i -propylthio and n -, i -, sec - and t -butylthio; halogenoalkyl, halogenoalkoxy and halogenoalkylthio preferably having 1 to 4, in particular 1 or 2 carbon atoms and preferably 1 to 9, in particular 1 to 5, halogen atoms, the halogen atoms being identical or different and preferably being fluorine, chlorine or bromine, in particular fluorine, such as trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy and trifluoromethylthio; hydroxyl; halogen, preferably fluorine, chlorine, bromine and iodine, in particular fluorine, chlorine and bromine; cyano; nitro; dialkylamino preferably having 1 to 4, in particular 1 or 2,carbon atoms per alkyl group, such as dimethylamino and diethylamino; carboxyl; alkylalkoxy having 1 to 4, in particular 1 or 2 carbon atoms in each alkyl moiety; carbonylalkoxy having 1 to 4, in particular 1 or 2 carbon atoms in the alkyl moiety, such as carbonylmethoxy and carbonylethoxy; carbonylalkyl having 1 to 4, in particular 1 or 2 carbon atoms in the alkyl moiety, such as acetyl and propionyl; formyl; carbonylaryloxy having 5 to 10 carbon atoms in the aryl moiety, such as carbonylphenoxy; carbonylaryl having 6 to 10 carbon atoms in the aryl moiety, such as benzoyl; oxycarbonylalkyl having 1 to 4, in particular 1 or 2,carbon atoms in the alkyl moiety, such as acetoxy; oxycarbonylaryl having 6 to 10 carbon atoms in the aryl moiety, such as benzoyloxy; carboxylamino, carbonylaminoalkyl, carbonylaminodialkyl, aminocarbonyl, alkylaminocarbonyl, aminocarbonylalkyl and alkylaminocarbonylalkyl each having 1 to 4, in particular 1 or 2 carbon atoms in the alkyl moiety; sulphonamido; sulphonalkyl; sulphonylalkyl and sulphonylalkoxy each having 1 to 4, in particular 1 or 2 carbon atoms; phenyl or phenoxy, in each case unsubstituted or substituted by halogen, in particular fluorine, chlorine and/or bromine.

In the general formulae, $R^1$, $R^2$, $R^3$ and $R^5$ independently of one another preferably represent methyl or ethyl and in particular hydrogen.

The definitions given here also apply in a corresponding manner to the definitions in the following preferred combinations of radicals.

Preferred compounds of the formula (I) are those in which $R^1$, $R^2$, $R^3$, $R^4$, $R^5$ and $R^6$ are identical or different and represent hydrogen or straight-chain or branched alkyl having 1 to 6 carbon atoms, or $R^3$ and $R^4$ together with the carbon atom to which they are bonded, form a cycloalkyl ring having 3 to 7 carbon atoms, and Ar and Ar' are identical or different and represent phenyl, pyridyl or furyl, in each case unsubstituted or substituted, or phenylalkyl which is unsubstituted or substituted in the phenyl moiety and which has 1 to 4 carbon atoms in the straight-chain or branched alkyl moiety, suitable substituents in the phenyl moiety in each case being: alkyl, alkoxy and alkylthio each having 1 to 4 carbon atoms; halogenoalkyl, halogenoalkoxy and halogenoalkylthio each having 1 to 4 carbon atoms and 1 to 9 halogen atoms, the halogen atoms being identical or different; hydroxyl; halogen; cyano; nitro; dialkylamino having 1 to 4 carbon atoms per alkyl group; carboxyl; alkylalkoxy having 1 to 4 carbon atoms in each alkyl moiety; carbonylalkoxy having 1 to 4 carbon atoms in the alkyl moiety; carbonylalkyl having 1 to 4 carbon atoms in the alkyl moiety; formyl; carbonylaryloxy having 5 to 10 carbon atoms in the aryl moiety; carbonylaryl having 6 to 10 carbon atoms in the aryl moiety; oxycarbonylalkyl having 1 to 4 carbon atoms in the alkyl moiety; oxycarbonylaryl having 6 to 10 carbon atoms in the aryl moiety; carbonylamino, carbonylaminoalkyl, carbonylaminodialkyl, aminocarbonyl, alkylaminocarbonyl, aminocarbonylalkyl and alkylaminocarbonylalkyl each having 1 to 4 carbon atoms in the alkyl moiety; sulphonamido; sulphonalkyl; sulphonylalkyl and sulphonylalkoxy each having 1 to 4 carbon atoms; phenyl or phenoxy, in each case unsubstituted or substituted by halogen.

Particularly preferred compounds of the formula (I) are those in which $R^1$ represents hydrogen and $R^2$, $R^3$ and $R^4$ are identical or different and represent hydrogen or straight-chain or branched alkyl having 1 to 5 carbon atoms, or $R^3$ and $R^4$, together with the carbon atom to which they are bonded, form a cycloalkyl ring having 3 to 6 carbon atoms, $R^5$ and $R^6$ are identical or different and represent hydrogen, methyl or ethyl, Ar represents phenyl which is unsubstituted or monosubstituted to trisubstituted by identical or different substituents, suitable substituents being the following: alkyl, alkoxy and alkylthio each having 1 or 2 carbon atoms; halogenoalkyl, halogenoalkoxy and halogenoalkylthio having 1 or 2 carbon atoms and 1 to 5 halogen atoms, the halogen atoms being identical or different; hydroxyl; fluorine, chlorine, bromine and iodine; cyano; nitro; dialkylamino having 1 or 2 carbon atoms per alkyl group; carboxyl; alkylalkoxy having 1 or 2 carbon atoms in each alkyl moiety; carbonylalkoxy having 1 or 2 carbon atoms in the alkyl moiety; carbonylalkyl having 1 or 2 carbon atoms in the alkyl moiety; formyl; carbonylphenoxy; benzoyl; oxycarbonylalkyl having 1 or 2 carbon atoms; benzoyloxy; carbonylamino, carbonylaminoalkyl, carbonylaminodialkyl, aminocarbonyl, alkylaminocarbonyl, aminocarbonylalkyl and alkylaminocarbonylalkyl each having 1 or 2 carbon atoms in the alkyl moiety; sulphonamido; sulphonalkyl, sulphonylalkyl and sulphonylalkoxy each having 1 or 2 carbon atoms; phenyl or phenoxy, in each case unsubstituted or substituted by fluorine, chlorine or bromine, and Ar' represents phenyl, pyridyl or furyl, in each case unsubstituted or monosubstituted to trisubstituted by identical or different substituents, or represents phenylalkyl which is unsubstituted or monosubstituted to trisubstituted in the phenyl moiety by identical or different substituents and has 1 or 2 carbon atoms in the alkyl moiety, suitable phenyl substituents in each case being the abovementioned phenyl substituents.

Very particularly preferred compounds of the formula (I) are those in which $R^1$ represents hydrogen, $R^2$ represents hydrogen or methyl, $R^3$ and $R^4$ are identical or different and represent hydrogen, methyl, ethyl, n- or i-propyl, n-, i-, s- or t-butyl or 3-pentyl, or $R^3$ and $R^4$, together with the carbon atom to which they are bonded, form a cyclopropyl, cyclopentyl or cyclohexyl ring, $R^5$ represents hydrogen or methyl, $R^6$ represents hydrogen, methyl or ethyl, Ar represents phenyl which is unsubstituted, or monosubstituted or disubstituted by identical or different substituents, suitable substituents being the following: methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, totrafluoroethoxy, trifluorochloroethoxy, trifluoromethoxy, trifluoromethylthio, chlorine, bromine, fluorine, nitro and cyano, and Ar' represents benzyl or 1,2-phenethyl which are unsubstituted, or monosubstituted or disubstituted in the phenyl moiety by identical or different substituents, but in particular phenyl which is unsubstituted, or monosubstituted or disubstituted by identical or different substituents, suitable phenyl substituents in each case being the abovementioned phenyl substituents.

Especially preferred substituted amino acid amide derivatives of the general formula (I) are those in which $R^1$, $R^2$, $R^5$, $R^6$, Ar and Ar' have the meanings given above, in particular those in the preferred ranges, $R^3$ represents hydrogen and $R^4$ represents methyl, ethyl, n-propyl, t-butyl, i-butyl or 3-pentyl, in particular i-propyl or s-butyl or $R^3$ and $R^4$, together with the carbon atom to which they are bonded, form a cycloalkyl ring having 3 to 6 carbon atoms, in particular a cyclopropyl, cyclopentyl or cyclohexyl ring.

The substituted amino acid amide derivatives of the general formula (I)

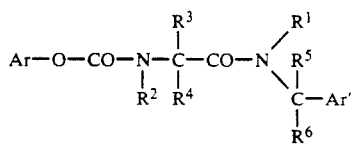

in which $R^1$, $R^2$, $R^3$, $R^4$, $R^5$, $R^6$, Ar and Ar' have the abovementioned meanings, are obtained when a substituted amino acid of the formula (II)

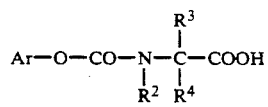

in which Ar, $R^2$, $R^3$ and $R^4$ have the abovementioned meanings or their carboxyl-activated derivatives, if appropriate in the presence of a catalyst, if appropriate in the presence of an acid-binding agent and if appropriate in the presence of a diluent, is reacted with an amine of the formula (III)

$$HNR^1-CR^5R^6Ar' \qquad (III)$$

in which Ar', $R^1$, $R^5$ and $R^6$ have the abovementioned meanings.

If, for example, phenoxycarbonyl-L-isoleucine and 1-(4-chlorophenyl)-ethylamine are used as starting materials, the course of the process according to the invention can be represented by the following equation:

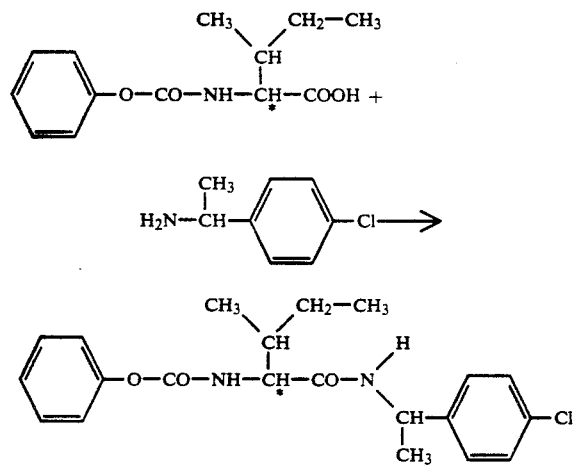

Formula (II) provides a general definition of the amino acid derivatives to be used as starting materials for carrying out the process according to the invention. In this formula, Ar, $R^2$, $R^3$ and $R^4$ preferably have the meanings which have already been mentioned as preferred for these substituents in connection with the description of the substances of the formula (I) according to the invention.

The amino acid derivatives of the formula (II) are generally known (compare, for example, Houben-Weyl, Methoden der organischen Chemie [Methods of Organic Chemistry], Volume XV, part 1 and 2, pages 46 et seq. and 112 et seq., Georg Thieme Verlag, Stuttgart 1974; D. Keller et al., Org. Synth. 60, 2145 (1981); and R. C. Sheppard, A Specialist Periodical Report, Aminoacids, Peptides and Proteins, The Royal Society of Chemistry, Burlington House, London 1978, and I.P. Greenstein and M. Winitz, Chemistry of Amino Acids, I. Wiley Sons Inc., New York, London 1961; and E. Schröder and K. Lübke, The Peptides Vol. I, Academic Press, New York, London 1965) or can be obtained by the methods indicated therein.

The carboxyl-activated derivatives of the amino acid of the formula (II) additionally to be used as starting materials for carrying out the process according to the invention are generally known.

Suitable carboxyl-activated derivatives of the amino acids of the formula (II) are all carboxyl-activated derivatives, such as acid halides, such as, for example, acid chlorides and acid azides, in addition symmetrical and mixed anhydrides, such as, for example, the mixed o-alkylcarbonic acid anhydrides, furthermore activated esters, such as, for example, p-nitrophenyl esters or N-hydroxysuccinimide esters and also activated forms of the amino acids generated in situ using condensing agents, such as, for example, dicyclohexylcarbodiimide or carbonyldiimidazole.

The acid chlorides and mixed anhydrides corresponding to the amino acids of the formula (II) are preferably employed. They can be prepared by reacting the amino acids of the formula (II) or their salts with a halogenating agent or one of the generally known agents for the preparation of mixed anhydrides, such as, for example, phosphorus pentachloride, thionyl chloride, oxalyl chloride or isobutyl chloroformate, in a generally known manner. The use of isobutyl chloroformate is preferred.

The reaction can be carried out in the presence of inert diluents such as, for example, aromatic, non-aromatic or halogenated hydrocarbons such as, for example, methylene chloride and toluene; ketones, such as, for example, acetone; esters, such as, for example, ethyl acetate; amides, such as, for example, dimethylformamide; nitriles, such as, for example, acetonitrile; or ethers, such as, for example, tetrahydrofuran or its mixtures and/or in the presence of an acid-binding agent, such as, preferably, a tertiary amine, such as, for example, triethylamine, pyridine or N-methylpiperidine, at temperatures of $-78°$ C. to $100°$ C., preferably $-60°$ C. to $25°$ C.

Formula (III) provides a general definition of the amines additionally to be used as starting materials for carrying out the process according to the invention. In this formula, $R^1$, Ar', $R^5$ and $R^6$ have the abovementioned meanings.

The amines of the formula (III) are generally known compounds of organic chemistry.

Suitable diluents for the process according to the invention are inert organic solvents such as: ketones, such as acetone or ethyl methyl ketone; esters such as ethyl acetate or methyl acetate; amides such as dimethylformamide; nitriles, such as acetonitrile; chlorohydrocarbons, such as methylene chloride or carbon tetrachloride; hydrocarbons, such as toluene or ethers, such as tetrahydrofuran and also, if appropriate, water and its mixtures.

Suitable acid-binding agents for the process according to the invention are customary inorganic and organic acid-binders. These preferably include tertiary amines, such as triethylamine, pyridine or N-methylpiperidine, and also inorganic bases, for example metal hydroxides such as sodium hydroxide and potassium hydroxide or metal carbonates such as sodium carbonate or calcium carbonate.

The process according to the invention is optionally carried out in the presence of a catalyst. Examples which may be mentioned are 4-dimethylaminopyridine, 1-hydroxybenzotriazole or dimethylformamide.

The temperatures can be varied within a relatively wide range when carrying out the process. In general, the process is carried out at $-78°$ to $+120°$ C., preferably at $-60°$ to $+40°$ C.

When carrying out the process according to the invention, equimolar amounts are preferably used.

In this connection, the amino acid derivatives of the formula (II) are employed as pure optical isomers (D or L-form) or as racemates.

The invention includes both the pure isomers and the mixtures. These mixtures can be separated into the components by conventional methods, for example selective crystallization from suitable solvents or chromatography on silica gel or alumina. Racemates can be separated into the individual enantiomers by customary methods, thus, for example, by salt formation with optically active acids such as camphor sulphonic acid or dibenzoyltartaric acid and selective crystallization or by derivatization with suitable optically active reagents, separation of the diastereomeric derivatives and recleavage or separation on optically active column material.

The active compounds of the formula (I) according to the invention have a strong action against pests and can be used for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae:*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be employed protectively and systemically with particularly good effect for combating Phytophthora species on tomatoes or Plasmopara species on vines and also for combating rice diseases, such as, for example, against the causative organism of rotten neck (*Pyricularia oryzae*) or against the causative organism of stem blight (*Pellicularia sasakii*).

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing-agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation Examples

Example 1

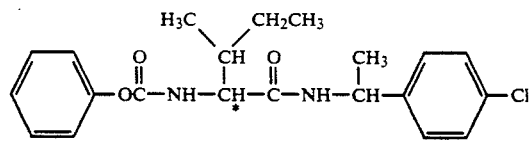

2.12 g (8.4 mmol) of phenoxycarbonyl-L-isoleucine are dissolved in 50 ml of THF/CH$_2$Cl$_2$ (1:9) and 0.83 g (8.4 mmol) of N-methylpiperidine is added at −20° C. After stirring for 5 minutes at −20° C., 1.15 g (8.4 mmol) of isobutyl chloroformate are allowed to drip in, the mixture is subsequently stirred at −20° C. for 10 minutes and cooled to −60° C., and 1.30 g (8.4 mmol) of 1-(4-chlorophenyl)ethylamine dissolved in 5 ml of THF/CH$_2$Cl$_2$ (1:9) are added. The mixture is subsequently stirred at −15° C. for 2 hours and then at room temperature for a further 15 hours. For working-up, the precipitate is filtered off, the solution is concentrated in vacuo and the residue is taken up in CH$_2$Cl$_2$. The organic phase is washed successively with water, NaHCO$_3$ solution and water, dried over Na$_2$SO$_4$ and freed of solvent in vacuo. 2.30 g (71% of theory) of colorless N$^2$-phenoxycarbonyl-N$^1$-[rac.-1-(4-chlorophenyl)-ethyl]-L-isoleucinamide having a melting point of 150°–156° C. are obtained.

The following compounds of the formula (I)

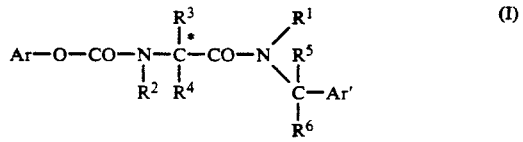

are obtained analogously to Example 1.

TABLE 1

| No. | Ar | $R^2$ | $R^3$ | $R^4$ | $R^1$ | $R^5$ | $R^6$ | Ar' | Melting point | * |
|---|---|---|---|---|---|---|---|---|---|---|
| 2 | phenyl | H | H | —CH(CH$_3$)$_2$ | H | H | CH$_3$ | 4-Cl-phenyl | 101–102° C. | L |
| 3 | 4-Cl-phenyl | H | H | —CH(CH$_3$)$_2$ | H | H | H | 4-Cl-phenyl | 191–192° C. | L |
| 4 | 4-Cl-phenyl | H | H | —CH(CH$_3$)$_2$ | H | H | CH$_3$ | 4-Cl-phenyl | 154–155° C. | L |
| 5 | 4-CH$_3$OOC-phenyl | H | H | —CH(CH$_3$)$_2$ | H | H | H | 4-Cl-phenyl | 192–193° C. | L |
| 6 | 4-CH$_3$OOC-phenyl | H | H | —CH(CH$_3$)$_2$ | H | CH$_3$ | H | 4-Cl-phenyl | 154–155° C. | L |
| 7 | 4-CH$_3$O-phenyl | H | H | —CH(CH$_3$)$_2$ | H | H | CH$_3$ | 4-CH$_3$-phenyl | 178–182° C. | L |
| 8 | 4-CH$_3$O-phenyl | H | H | —CH(CH$_3$)$_2$ | H | H | CH$_3$ | 4-OCH$_3$-phenyl | 161–165° C. | L |
| 9 | 4-CH$_3$O-phenyl | H | H | —CH(CH$_3$)$_2$ | H | H | CH$_3$ | 4-Cl-phenyl | 183–185° C. | L |

TABLE 1-continued

| No. | Ar | R² | R³ | R⁴ | R¹ | R⁵ | R⁶ | Ar' | Melting point | * |
|---|---|---|---|---|---|---|---|---|---|---|
| 10 | 4-CH₃O-C₆H₄- | H | H | -CH-CH₂-CH₃<br>       |<br>      CH₃ | H | H | CH₃ | 4-Cl-C₆H₄- | 168–170° C. | L |
| 11 | 4-Br-C₆H₄- | H | H | -CH(CH₃)₂ | H | H | CH₃ | 4-CH₃-C₆H₄- | 162–163° C. | L |
| 12 | 4-Br-C₆H₄- | H | H | -CH(CH₃)₂ | H | H | CH₃ | 4-OCH₃-C₆H₄- | 163–165° C. | L |
| 13 | 4-Br-C₆H₄- | H | H | -CH(CH₃)₂ | H | H | CH₃ | 4-Cl-C₆H₄- | 164–166° C. | L |
| 14 | 4-F-C₆H₄- | H | H | -CH(CH₃)₂ | H | H | CH₃ | 4-CH₃-C₆H₄- | 169–170° C. | L |
| 15 | 4-F-C₆H₄- | H | H | -CH(CH₃)₂ | H | H | CH₃ | 4-OCH₃-C₆H₄- | 172–173° C. | L |
| 16 | 4-F-C₆H₄- | H | H | -CH(CH₃)₂ | H | H | CH₃ | 4-Cl-C₆H₄- | 165–168° C. | L |
| 17 | 4-CH₃O-C₆H₄- | H | H | -CH(CH₃)₂ | H | H | CH₃ | 4-OCH₃-C₆H₄- | 163–168° C. | D/L |

TABLE 1-continued
| No. | Ar | $R^2$ | $R^3$ | $R^4$ | $R^1$ | $R^5$ | $R^6$ | Ar' | Melting point | * |
|---|---|---|---|---|---|---|---|---|---|---|
| 18 | 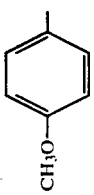 (CH₃O-) | H | H | —CH(CH₃)₂ | H | H | CH₃ | 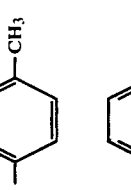 (-Cl) | 134–135° C. | D/L |
| 19 |  (CH₃O-) | H | H | —CH—CH₂—CH₃<br>    \|<br>    CH₃ | H | H | CH₃ |  (-OCH₃) | 159–163° C. | L |
| 20 |  (CH₃O-) | H | H | —CH(CH₃)₂ | H | H | —CH₂—CH₃ | 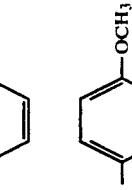 (-OCH₃) | 149–151° C. | D/L |
| 21 | 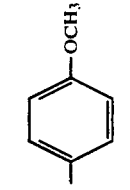 (CH₃-) | H | H | —CH(CH₃)₂ | H | H | CH₃ |  (-CH₃) | 179–182° C. | L |
| 22 |  (CH₃O-) | H | H | —CH—CH₂—CH₃<br>    \|<br>    CH₃ | H | H | CH₃ | 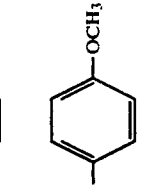 (-CH₃) | 168–170° C. | L |
| 23 | 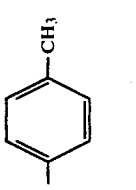 | H | H | —CH(CH₃)₂ | H | H | CH₃ |  (-OCH₃) | 170–175° C. | L |
| 24 |  (CH₃-) | H | H | —CH(CH₃)₂ | H | H | —CH₂CH₃ |  (-OCH₃) | 170–175° C. | L |
| 25 | 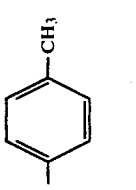 | H | H | —CH(CH₃)₂ | H | H | —CH₂CH₃ |  (-OCH₃) | 172–176° C. | L |

TABLE 1-continued

| No. | Ar | R² | R³ | R⁴ | R¹ | R⁵ | R⁶ | Ar' | Melting point | * |
|---|---|---|---|---|---|---|---|---|---|---|
| 26 | phenyl | H | H | —CH(CH₃)₂ | H | H | CH₃ | 4-methylphenyl | 170–175° C. | L |
| 27 | phenyl | H | H | —CH(CH₃)₂ | H | H | CH₃ | 4-methylphenyl | 158–162° C. | D/L |
| 28 | phenyl | H | H | —CH(CH₃)₂ | H | H | CH₃ | 4-methoxyphenyl | 158–162° C. | D/L |
| 29 | phenyl | H | H | —CH(CH₃)₂ | H | H | CH₃ | 4-chlorophenyl | 175–179° C. | D/L |
| 30 | phenyl | H | H | —CH(CH₃)₂ | H | H | CH₃ | 4-methoxyphenyl | 158–162° C. | D/L |
| 31 | phenyl | H | H | —CH—CH₂—CH₃ <br> \| <br> CH₃ | H | H | —CH₂CH₃ | 4-methylphenyl | 155–169° C. | L |
| 32 | phenyl | H | H | —CH—CH₂—CH₃ <br> \| <br> CH₃ | H | H | CH₃ | 4-methoxyphenyl | 154–161° C. | L |
| 33 | 4-methylphenyl | H | H | —CH(CH₃)₂ | H | H | CH₃ | 4-chlorophenyl | 126–127° C. | L |

TABLE 1-continued
| No. | Ar | R² | R³ | R⁴ | R¹ | R⁵ | R⁶ | Ar' | Melting point | * |
|---|---|---|---|---|---|---|---|---|---|---|
| 34 | 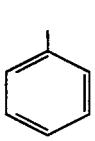 | H | H | —CH—CH₂—CH₃<br>\|<br>CH₃ | H | H | —CH₂CH₃ |  OCH₃ | 145–150° C. | L |
| 35 | 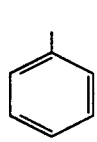 | H | H | —CH(CH₃)₂ | H | H | —CH₂CH₃ |  CH₃ | 150–156° C. | L |
| 36 |  | H | H | —CH(CH₃)₂ | H | H | —CH₂CH₃ |  Cl | 146–149° C. | L |
| 37 |  | H | H | —CH(CH₃)₂ | H | H | CH₃ | 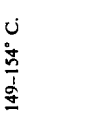 OCH₂CH₃ | 149–154° C. | L |
| 38 |  | H | H | —CH(CH₃)₂ | H | H | CH₃ | 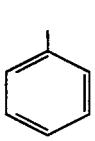 CH₂CH₃ | 158–160° C. | L |
| 39 | 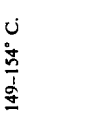 | H | H | —CH(CH₃)₂ | H | H | CH₃ | 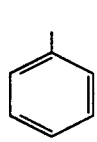 CH₂CH₃ | 112–135° C. | D/L |
| 40 | 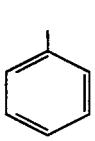 | H | H | —CH(CH₃)₂ | H | H | CH₃ |  OCH₂CH₃ | 121–137° C. | D/L |
| 41 | 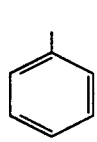 | H | H | —CH(CH₃)₂ | H | H | —CH₂CH₃ |  Cl | 155–172° C. | D/L |

TABLE 1-continued

| No. | Ar | $R^2$ | $R^3$ | $R^4$ | $R^1$ | $R^5$ | $R^6$ | Ar' | Melting point | * |
|---|---|---|---|---|---|---|---|---|---|---|
| 42 | phenyl | H | H | —CH(CH$_3$)$_2$ | H | H | —CH$_2$CH$_3$ | 4-CH$_3$-phenyl | 138–140° C. | D/L |
| 43 | 4-CH$_3$O-phenyl | H | H | —CH(CH$_3$)$_2$ | H | H | CH$_3$ | 4-CH$_3$-phenyl | 149–159° C. | D/L |
| 44 | 4-CH$_3$O-phenyl | H | H | —CH(CH$_3$)$_2$ | H | H | CH$_3$ | 4-CH$_2$CH$_3$-phenyl | 148–155° C. | D/L |
| 45 | 4-CH$_3$O-phenyl | H | H | —CH(CH$_3$)$_2$ | H | H | CH$_3$ | 4-Cl-phenyl | 149–163° C. | D/L |
| 46 | 4-CH$_3$O-phenyl | H | H | —CH(CH$_3$)$_2$ | H | H | —CH$_2$CH$_3$ | 4-CH$_3$-phenyl | 146–158° C. | D/L |
| 47 | phenyl | H | H | —CH(CH$_3$)$_2$ | H | H | —CH$_2$CH$_3$ | 4-Cl-phenyl | 151–153° C. | D/L |
| 48 | phenyl | H | H | —CH(CH$_3$)$_2$ | H | H | CH$_3$ | 4-OCH$_3$-phenyl | 140–143° C. | D/L |
| 49 | phenyl | H | H | —CH(CH$_3$)$_2$ | H | H | CH$_3$ | —(CH$_2$)$_2$-(4-OCH$_3$-phenyl) | 143–151° C. | D/L |

TABLE 1-continued
| No. | Ar | R² | R³ | R⁴ | R¹ | R⁵ | R⁶ | Ar' | Melting point | * |
|---|---|---|---|---|---|---|---|---|---|---|
| 50 | 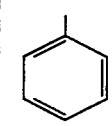 | H | H | —CH(CH₃)₂ | H | H | CH₃ | 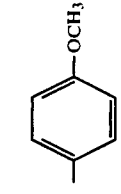 | 138–148° C. | L |
| 51 | 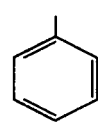 | H | H | —CH(CH₃)₂ | H | H | CH₃ | 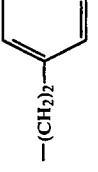 | 145–153° C. | L |
| 52 | 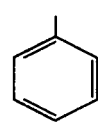 | H | H | —CH(CH₃)₂ | H | H | CH₃ | 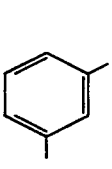 | 120–129° C. | L |
| 53 | 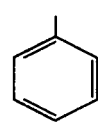 | H | H | —CH(CH₃)₂ | H | H | CH₃ | 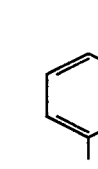 | 152–158° C. | L |
| 54 | 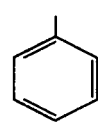 | H | H | —CH(CH₃)₂ | H | H | CH₃ | 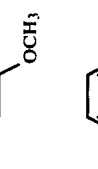 | 133–138° C. | D/L |
| 55 | 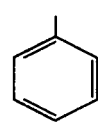 | H | H | —CH(CH₃)₂ | H | H | CH₃ | 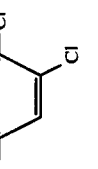 | 168–177° C. | D/L |
| 56 | 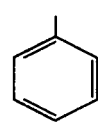 | H | H | —CH(CH₃)₂ | H | H | CH₃ | 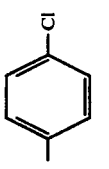 | 166–169° C. R-Amine | L |

TABLE 1-continued
| No. | Ar | $R^2$ | $R^3$ | $R^4$ | $R^1$ | $R^5$ | $R^6$ | Ar' | Melting point | * |
|---|---|---|---|---|---|---|---|---|---|---|
| 57 | 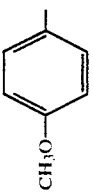 | H | H | —CH(CH$_3$)$_2$ | H | H | CH$_3$ | 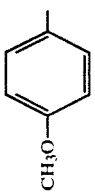 | 153–165° C. | D/L |
| 58 |  | H | H | —CH(CH$_3$)$_2$ | H | H | CH$_3$ | 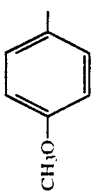 | 143–147° C. | D/L |
| 59 | 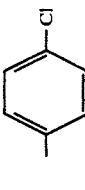 | H | H | —CH(CH$_3$)$_2$ | H | H | CH$_3$ | 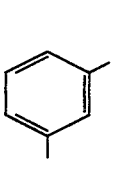 | 129–130° C. | D/L |
| 60 |  | H | H | —CH(CH$_3$)$_2$ | H | H | CH$_3$ | 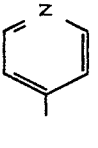 | 152–155° C. | D/L |
| 61 |  | H | H | —CH(CH$_3$)$_2$ | H | H | CH$_3$ |  | 138° C. (R+)-Amine | L |
| 62 |  | H | | —CH$_2$—CH$_2$—CH$_2$—CH$_2$— | H | H | CH$_3$ | 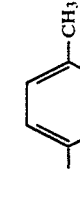 | 158° C. | |
| 63 | 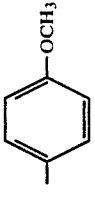 | H | | —CH$_2$—CH$_2$—CH$_2$—CH$_2$— | H | H | CH$_3$ |  | 164° C. | |
| 64 | | H | | —CH$_2$—CH$_2$—CH$_2$—CH$_2$— | H | H | CH$_3$ | | 178° C. | |

TABLE 1-continued
| No. | Ar | R² | R³ | R⁴ | R¹ | R⁵ | R⁶ | Ar' | Melting point | * |
|---|---|---|---|---|---|---|---|---|---|---|
| 65 | 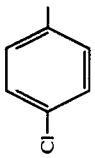 (4-Cl-C₆H₄) | H | H | —CH(CH₃)₂ | H | H | CH₃ |  (4-OCH₃-C₆H₄) | 168–170° C. | L |
| 66 | 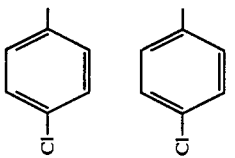 (4-Cl-C₆H₄) | H | H | —CH(CH₃)₂ | H | H | CH₃ |  (4-CH₃-C₆H₄) | 152° C. | L |
| 67 |  (4-Cl-C₆H₄) | H | H | —CH(CH₃)₂ | H | H | CH₃ |  (4-Cl-C₆H₄) | 179° C. (R+)-Amine | L |
| 68 |  (4-Cl-C₆H₄) | H | H | —CH(CH₃)₂— | H | H | CH₃ | 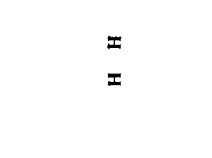 (4-C₂H₅-C₆H₄) | 159° C. | L |
| 69 |  (4-Cl-C₆H₄) | H | H | —CH(CH₃)₂ | H | H | CH₃ |  (4-OC₂H₅-C₆H₄) | 164° C. | L |
| 70 |  (C₆H₅) | H | H | —C₄H₉n | H | H | CH₃ | 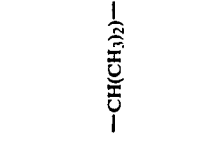 (4-Cl-C₆H₄) | 133° C. | L |
| 71 |  (C₆H₅) | H | H | —C₄H₉n | H | H | CH₃ |  (4-CH₃-C₆H₄) | 120° C. | L |
| 72 | 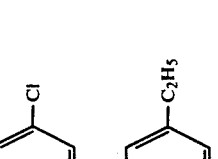 (C₆H₅) | H | H | —C₄H₉n | H | H | CH₃ | 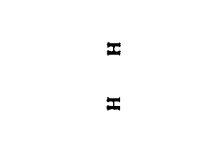 (4-OCH₃-C₆H₄) | 141° C. | L |

TABLE 1-continued
| No. | Ar | R² | R³ | R⁴ | R¹ | R⁵ | R⁶ | Ar' | Melting point | * |
|---|---|---|---|---|---|---|---|---|---|---|
| 73 | 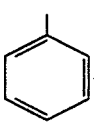 | H | H | —C₄H₉b | H | H | CH₃ | 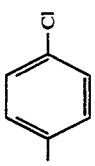 (Cl) | 132° C. | L |
| 74 |  | H | H | —C₄H₉n | H | H | CH₃ | 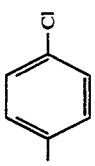 (CH₃) | 140° C. | L |
| 75 |  | H | H | —C₄H₉n | H | H | CH₃ | 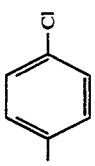 (OCH₃) | 136–139° C. | L |
| 76 |  | H | —CH₂—CH₂— | | H | H | CH₃ | 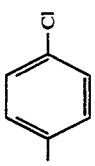 (Cl) | 145° C. | |
| 77 |  | H | —CH₂—CH₂— | | H | H | CH₃ | 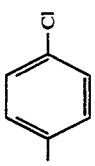 (CH₃) | 146° C. | |
| 78 | 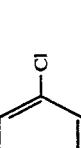 | H | —CH₂—CH₂— | | H | H | CH₃ | 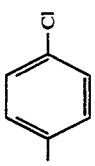 (OCH₃) | 133° C. | L |
| 79 |  | H | H | —C₄H₉t | H | H | CH₃ | 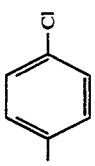 (Cl) | 154° C. | D/L |
| 80 |  | H | H | —C₄H₉t | H | H | CH₃ | 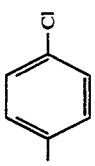 (CH₃) | 155° C. | D/L |

TABLE 1-continued
| No. | Ar | R² | R³ | R⁴ | R¹ | R⁵ | R⁶ | Ar' | Melting point | * |
|---|---|---|---|---|---|---|---|---|---|---|
| 81 | 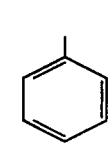 | H | H | —C₄H₉ₜ | H | H | CH₃ | 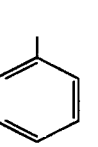 (4-OCH₃) | 152° C. | D/L |
| 82 | 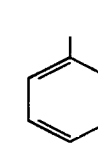 | H | H | —C₂H₅ | H | H | CH₃ | 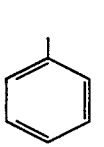 (4-Cl) | 135° C. | L |
| 83 | 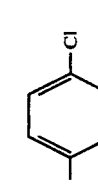 | H | H | —C₂H₅ | H | H | CH₃ | 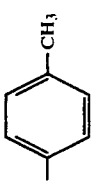 (4-CH₃) | 143° C. | L |
| 84 | 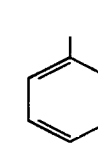 | H | H | —C₂H₅ | H | H | CH₃ | 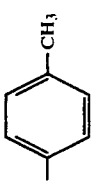 (4-OCH₃) | 140° C. | L |
| 85 | 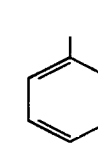 | H | H | —CH—(CH₃)₂ | H | H | CH₃ | 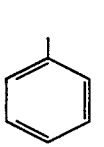 (4-C₂H₅) | 156-158° C. (R+)-Amine | L |
| 86 | 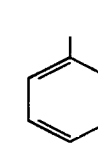 | H | H | —CH—(CH₃)₂ | H | H | CH₃ | 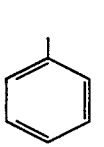 (4-CH₃) | 168-170° C. (R+)-Amine | L |
| 87 | 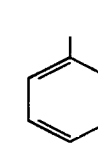 | H | H | —CH—(CH₃)₂ | H | H | CH₃ | 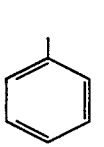 (4-OCH₃) | 166-168° C. (R+)-Amine | L |
| 88 | 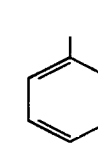 | H | H | —CH—(CH₃)₂ | H | H | CH₃ | 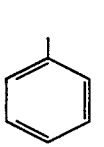 (4-C₄H₉ₜ) | 97° C. | L |

TABLE 1-continued

| No. | Ar | R² | R³ | R⁴ | R¹ | R⁵ | R⁶ | Ar' | Melting point | * |
|---|---|---|---|---|---|---|---|---|---|---|
| 89 | phenyl | H | H | —CH—(CH₃)₂ | H | H | CH₃ | 4-F-phenyl | 151° C. | L |
| 90 | phenyl | H | H | —CH—(CH₃)₂ | H | H | CH₃ | 3-pyridyl |  | L |
| 91 | phenyl | H | H | —CH—(CH₃)₂ | H | H | CH₃ | 4-SO₂CH₃-phenyl | 136° C. | L |
| 92 | phenyl | H | H | —CH—(CH₃)₂ | H | H | CH₃ | 3-CF₃-phenyl | 148° C. | L |
| 93 | phenyl | H | H | —CH—(CH₃)₂ | H | H | CH₃ | 2-furyl |  | L |
| 94 | phenyl | H | H | —CH—(CH₃)₂ | H | H | CH₃ | 4-OCF₃-phenyl | 142° C. | L |
| 95 | 4-CH₃O-phenyl | H | H | —CH—(CH₃)₂ | H | H | CH₃ | 4-C₂H₅-phenyl | 162° C. | L |
| 96 | 4-CH₃O-phenyl | H | H | —CH—(CH₃)₂ | H | H | CH₃ | 4-CH₃-phenyl | 159° C. (R+)-Amine | L |
| 97 | 4-CH₃O-phenyl | H | H | —CH—(CH₃)₂ | H | H | CH₃ | 4-OCH₃-phenyl | 181° C. (R+)-Amine | L |

Note: Row 97 shows 174° C. (R+)-Amine based on the third melting point entry; rows 95-97 correspond to 159°, 181°, 174° C. respectively.

Example A

Plasmopara Test (Vines)/Protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100 % relative atmospheric humidity for 1 day. The plants are then placed in a greenhouse at 22° C. and about 80 % atmospheric humidity for 5 days. The plants are then moistened and placed in a humidity chamber for 1 day.

Evaluation is carried out 7 days after the inoculation.

Thus, in this test, for example, the compounds according to Preparation Examples (1), (2), (4), (6), (8), (9), (10), (11), (12), (13) and (14) exhibit an excellent degree of action at an exemplary active compound concentration of 5 ppm.

Phytophthora Test (Tomato)/Protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and at about 20° C.

Evaluation is carried out 3 days after the inoculation.

For example,-the compounds according to Preparation Examples (1), (4), (7) and (8) to (16) show an excellent degree of action at an exemplary active compound concentration of 5 ppm.

It is understood that the specification and examples are illustrative but not limitative of the present invention and that other embodiments within the spirit and scope of the invention will suggest themselves to those skilled in the art.

We claim:

1. An amino acid amide of the formula

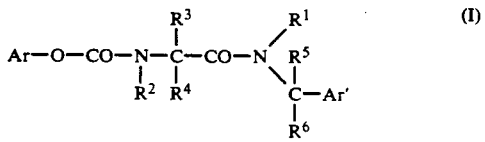

(I)

in which

Ar and Ar' are identical or different and represent unsubstituted or substituted aryl, unsubstituted or substituted aralkyl, unsubstituted or substituted heteroaryl and unsubstituted or substituted heteroarylalkyl, the heteroaryl radical or heteroaryl moiety of the heteroarylalkyl radical being monocyclic with a single hetero atom selected from the group consisting of O, N, and S, and $R^1$, $R^2$, $R^3$, $R^4$, $R^5$, $R^6$ are identical or different and represent hydrogen or alkyl or $R^3$ and $R^4$, together with the carbon atom to which they are bonded, form a cycloalkyl ring.

2. An amino acid amide according to claim 1, in which $R^1$, $R^2$, $R^3$, $R^4$, $R^5$, $R^6$ are identical or different and represent hydrogen or straight-chain or branched alkyl having 1 to 6 carbon atoms, or $R^3$ and $R^4$, together with the carbon atom to which they are bonded, form a cycloalkyl ring having 3 to 7 carbon atoms, and Ar and Ar' are identical or different and represent phenyl, furyl or pyridyl, in each case unsubstituted or substituted, or phenylalkyl which is unsubstituted or substituted in the phenyl moiety and which has 1 to 4 carbon atoms in the straight-chain or branched alkyl moiety, the substituents on the phenyl moiety in each case being selected from the group consisting of alkyl, alkoxy and alkylthio each having 1 to 4 carbon atoms; halogenoalkyl, halogenoalkoxy and halogenoalkylthio each having 1 to 4 carbon atoms and 1 to 9 halogen atoms, the halogen, atoms being identical or different; hydroxyl; halogen; cyano; nitro; dialkylamino having 1 to 4 carbon atoms per alkyl group; carboxyl; alkylalkoxy having 1 to 4 carbon atoms in each alkyl moiety; carbonylalkoxy having 1 to 4 carbon atoms in the alkyl moiety; carbonylalkyl having 1 to 4 carbon atoms in the alkyl moiety; formyl; carbonylaryloxy having 5 to 10 carbon atoms in the aryl moiety; carbonylaryl having 6 to 10 carbon atoms in the aryl moiety; oxycarbonylalkyl having 1 to 4 carbon atoms in the alkyl moiety; oxycarbonylaryl having 6 to 10 carbon atoms in the aryl moiety; carbonylamino, carbonylaminoalkyl, carbonylaminodialkyl, aminocarbonyl, alkylaminocarbonyl, aminocarbonylalkyl and alkylaminocarbonylalkyl each having 1 to 4 carbon atoms in the alkyl moiety; sulphonamido; sulphonalkyl; sulphonylalkyl and sulphonylalkoxy each having 1 to 4 carbon atoms; phenyl or phenoxy, in each case unsubstituted or substituted by halogen.

3. An amino acid amide according to claim 1, in which $R^1$ represents hydrogen and $R^2$, $R^3$ and $R^4$ are identical or different and represent hydrogen or straight-chain or branched alkyl having 1 to 5 carbon atoms, or $R^3$ and $R^4$, together with the carbon atom to which they are bonded, form a cycloalkyl ring having 3 to 6 carbon atoms, $R^5$ and $R^6$ are identical or different and represent hydrogen, methyl or ethyl, and Ar represents phenyl which is unsubstituted or monosubstituted to trisubstituted by identical or different substituents selected from the group consisting of alkyl, alkoxy and alkylthio each having 1 or 2 carbon atoms; halogenoalkyl, halogenoalkoxy and halogenoalkylthio having 1 or 2 carbon atoms and 1 to 5 halogen atoms, the halogen atoms being identical or different; hydroxyl; fluorine, chlorine, bromine and iodine; cyano; nitro; dialkylamino having 1 or 2 carbon atoms per alkyl group; carboxyl; alkylalkoxy having 1 or 2 carbon atoms in each alkyl moiety; carbonylalkoxy having 1 or 2 carbon atoms in the alkyl moiety; carbonylalkyl having 1 or 2 carbon atoms in the alkyl moiety; formyl; carbonylphenoxy; benzoyl; oxycarbonylalkyl having 1 or 2 carbon atoms; benzoyloxy; carbonylamino, carbonylaminoalkyl, carbonylamino, carbonylaminodialkyl, aminocarbonyl, alkylaminocarbonyl, aminocarbonylalkyl and alkylaminocarbonylalkyl each having 1 or 2 carbon atoms in the alkyl moiety; sulphonamido; sulphonalkyl, sulphonylalkyl and sulphonylalkoxy each having 1 or 2 carbon atoms; and phenyl or phenoxy, in each case unsubstituted or substituted by fluorine, chlorine or bromine, and Ar' represents phenyl , furyl or pyridyl, in each case unsubstituted or monosubstituted to trisubstituted by identical or different substituents, or represents phenylalkyl which is unsubstituted or monosubstituted to trisubstituted in the phenyl moiety by identical or different substituents and has 1 or 2 carbon atoms in the alkyl moiety, the phenyl substituents in each case being the abovementioned phenyl substituents for Ar.

4. An amino acid amide according to claim 1, in which $R^1$ represents hydrogen, $R^2$ represents hydrogen or methyl, $R^3$ and $R^4$ are identical or different and represent hydrogen, methyl, ethyl, n- or i-propyl, n-, i-, s- or t-butyl or 3-pentyl, or $R^3$ and $R^4$, together with the carbon atom to which they are bonded, form a cyclopropyl, cyclopentyl or cyclohexyl ring, $R^5$ represents hydrogen or methyl, $R^6$ represents hydrogen, methyl or ethyl, and Ar represents phenyl which is unsubstituted, or monosubstituted or disubstituted by identical or different substituents selected from the group consisting of methyl, ethyl, n- and i-propyl, n-, i-, s- and t-butyl, methoxy, ethoxy, i- and n-propoxy, n-, i-, s- and t-butoxy, trifluoromethyl, difluoromethyl, pentafluoroethyl, tetrafluoroethyl, trifluorochloroethyl, trifluoroethyl, trifluoroethoxy, difluoromethoxy, pentafluoroethoxy, tetrafluoroethoxy, trifluorochloroethoxy, trifluoromethoxy, trifluoromethylthio, chlorine, bromine, fluorine, nitro and cyano, and Ar' represents benzyl, 1,2-phenethyl or phenyl which are unsubstituted, or monosubstituted or disubstituted in the phenyl moiety in each case by identical or different substituents, the phenyl substituents in each case being the abovementioned phenyl substituents for Ar.

5. An amino acid amide according to claim 4, in which $R^3$ represents hydrogen, and $R^4$ represents methyl, ethyl, n-propyl, t-butyl, i-propyl, i-butyl, s-butyl or 3-pentyl, or $R^3$ and $R^4$, together with the carbon atom to which they are bonded, form a cycloalkyl ring having 3 to 6 carbon atoms.

6. A fungicidal composition comprising a fungicidally effective amount of a compound according to claim 1 and a diluent.

7. A method of combating fungi which comprises applying to such fungi or to a fungus habitat a fungicidally effective amount of a compound according to claim 1.

* * * * *